United States Patent
Wyrobek (10) Patent No.: US 9,752,900 B2
(45) Date of Patent: Sep. 5, 2017

(54) MULTI-PLATE CAPACITIVE TRANSDUCER

(71) Applicant: Wyrobek International, Inc., Minnetonka, MN (US)

(72) Inventor: Jerzy Wyrobek, Cape Canaveral, FL (US)

(73) Assignee: Wyrobek International, Inc., Minnetonka, MN (US)

( * ) Notice: Subject to any disclaimer, the term of this patent is extended or adjusted under 35 U.S.C. 154(b) by 137 days.

(21) Appl. No.: 14/796,266

(22) Filed: Jul. 10, 2015

(65) Prior Publication Data
US 2017/0010129 A1    Jan. 12, 2017

(51) Int. Cl.
| | | |
|---|---|---|
| G01R 27/26 | (2006.01) | |
| G01R 31/08 | (2006.01) | |
| G01D 5/241 | (2006.01) | |
| G01D 5/24 | (2006.01) | |

(52) U.S. Cl.
CPC .......... *G01D 5/2417* (2013.01); *G01D 5/24* (2013.01); *G01R 27/2605* (2013.01)

(58) Field of Classification Search
CPC ....... G01R 27/26; G01D 5/24; G01D 5/24175
USPC ........................ 324/658, 686, 519
See application file for complete search history.

(56) References Cited

U.S. PATENT DOCUMENTS

| | | |
|---|---|---|
| 4,694,687 A | 9/1987 | Bonin et al. |
| 4,930,043 A | 5/1990 | Wiegand |
| 5,381,300 A | 1/1995 | Thomas et al. |
| 5,553,486 A | 9/1996 | Bonin |
| 5,576,483 A | 11/1996 | Bonin |
| 5,661,235 A | 8/1997 | Bonin |
| 5,869,751 A | 2/1999 | Bonin |
| 6,026,677 A | 2/2000 | Bonin |
| 7,046,497 B1 | 5/2006 | Bonin |
| 2007/0180924 A1 | 8/2007 | Warren et al. |
| 2009/0154053 A1 | 6/2009 | Biggs et al. |
| 2010/0242600 A1 | 9/2010 | Lin et al. |

FOREIGN PATENT DOCUMENTS

JP    2012147115 A    8/2012

OTHER PUBLICATIONS

International Search Report and Written Opinion from PCT Application Serial No. PCT/US2016/041332, dated Oct. 20, 2016, 15 pages.

*Primary Examiner* — Amy He
(74) *Attorney, Agent, or Firm* — Kinney & Lange, P.A.

(57) ABSTRACT

A capacitive transducer includes first and second fixed outer plates, each having fixed electrodes positioned on inner surfaces, and a center plate assembly positioned between the fixed outer plates. The center plate assembly includes a top center plate and bottom center plate. The top and bottom center plates each have an inner section, an outer frame positioned outward of a perimeter of the inner section, a set of springs connecting the outer frame to the inner section, and a center electrode positioned on an outer surface of the inner section. The set of springs has thickness less than each of the inner section and the outer frame. The center electrodes of the top and bottom center plates are connected to become electrically one electrode.

18 Claims, 8 Drawing Sheets

MULTI-PLATE CAPACITIVE TRANSDUCER

BACKGROUND

The present invention relates to a force imparting device and/or capacitor displacement sensor and more particularly to a multi-plate capacitive transducer.

Capacitive transducers have wide application, including use as pressure and displacement sensors, accelerometers, and micro indentation or micro hardness testing devices. Capacitive transducers offer several advantages, including high sensitivity and resolution. A multi-plate capacitive transducer with two layers of springs provides for parallel motion of the shared pick-up plate with respect to the upper and lower drive plates. Parallel motion is known to stabilize the total gap between the drive plates and the shared pick-up plate. Prior art devices of this configuration have included a separate spacer member to separate the drive plate and pick-up plate electrodes, which increases the complexity of assembly and the number of plates that must be bonded by adhesive, generally an epoxy. Some of the materials used in prior art devices, including the epoxy, can be sensitive to temperature and moisture, limiting the effectiveness of the sensor and/or lifetime of the device. The pick-up plates, which include the springs, are generally of a single thickness determined by the desired spring constant. Pick-up plates having a single thickness create a spring geometry more sensitive to deformation. Additionally, metal pick-up plates of the prior art devices have been manufactured from commercially available shim stock with relatively high manufacturing tolerances and spring stiffness variation.

A need exists for a multi-plate capacitive transducer with parallel motion that eliminates the use of epoxy adhesives, reduces the number of interfaces to simplify assembly, allows for improved manufacturing tolerances, is less susceptible to changes in humidity and temperature, and comprises springs that are less sensitive to unintended deformation.

SUMMARY

A capacitive transducer includes a first fixed outer plate having a first fixed electrode positioned on an inner surface, a second fixed outer plate having a second fixed electrode positioned on an inner surface, and a center plate assembly positioned between the first and second fixed outer plates. The center plate assembly includes a top center plate and bottom center plate. The top center plate has a first inner section, a first outer frame positioned outward of a perimeter of the first inner section, a first set of springs connecting the first outer frame to the first inner section, and a first center electrode positioned on an outer surface of the first inner section. The first set of springs has thickness less than each of the first inner section and the first outer frame. The bottom plate is a mirror image of the top center plate including a second inner section, a second outer frame positioned outward of a perimeter of the second inner section, a second set of springs connecting the second outer frame to the second inner section, and a second center electrode positioned on an outer surface of the second inner section. The second center electrode and the first center electrode are connected to become electrically one electrode.

In another embodiment, a capacitive transducer includes a first fixed outer plate having a first fixed electrode positioned on an inner surface, a second fixed outer plate having a second fixed electrode positioned on an inner surface, and a center plate assembly positioned between the first and second fixed outer plates. The center plate assembly includes a top center plate and a bottom center plate. The top center plate includes a first inner section, a first outer frame positioned outward of a perimeter of the first inner section, a first set of springs connecting the first outer frame to the first inner section, a first center electrode positioned on an outer surface of the first inner section, and a first spacer member extending upward from an outer surface of the first outer frame to separate the first center electrode from the first fixed electrode. The bottom center plate is a mirror image of the top center plate including a second inner section, a second outer frame positioned outward of a perimeter of the second inner section, a second set of springs connecting the second outer frame to the second inner section, a second center electrode positioned on an outer surface of the second inner section, and a second spacer member extending downward from an outer surface of the second outer frame to separate the second center electrode from the second fixed electrode. The second center electrode and the first center electrode are connected to become electrically one electrode. An inner surface of the top center plate and an inner surface of the bottom center plate are bonded together.

A method of making a capacitive transducer includes the steps of etching an outer surface of each of an upper and lower center plate to form a raised spacer member along a perimeter of the upper and lower center plates; etching through a full thickness of each of the upper and lower center plates to create an outer frame, inner section, and a plurality of springs connecting the outer frame to the inner section; depositing a layer of conducting material on the outer surface of the inner section of each of the upper and lower center plates; depositing a layer of conducting material on an inner surface of a first fixed outer plate and an inner surface of a second fixed outer plate; etching through a full thickness of a portion of each of the upper and lower center plates and the first and second fixed outer plates to create a centrally-located hole; glass frit bonding the first and second center plates together; and glass frit bonding the spacer members to inner surfaces of the first and second fixed outer plates.

The present summary is provided only by way of example, and not limitation. Other aspects of the present disclosure will be appreciated in view of the entirety of the present disclosure, including the entire text, claims and accompanying figures.

While the above-identified figures set forth embodiments of the present invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features, steps and/or components not specifically shown in the drawings.

DETAILED DESCRIPTION

Figure 1:
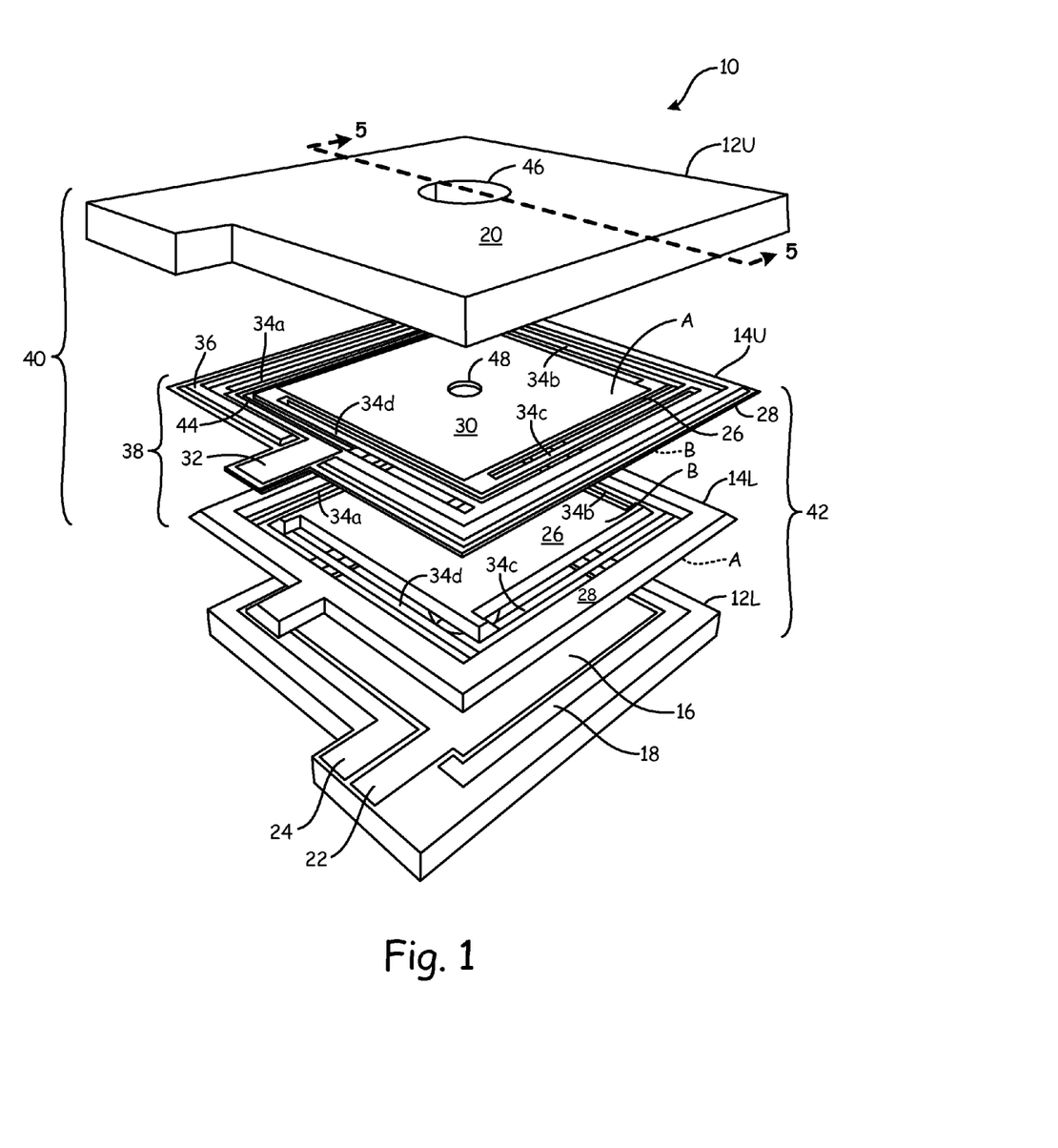
FIG. 1 is an exploded perspective view of a capacitive transducer device.

FIG. 1 is an exploded perspective view of multi-plate capacitive transducer device 10. Capacitor transducer device 10 includes fixed drive plates 12U and 12L (referring to upper and lower drive plates) and pick-up plates 14U and 14L (referring to upper and lower pick-up plates). Drive plate 12L can be a duplicate of drive plate 12U, flipped in orientation for assembly. Pick-up plate 14L can be a mirror image of pick-up plate 14U (i.e., side A of pick-up plate 14L is a minor image of side A of pick-up plate 14U, and side B of pick-up plate 14L is a minor image of side B of pick-up plate 14U). Drive plates 12U and 12L each have active electrode 16, shield electrodes 18 and 20, and connection terminals 22 and 24. Pick-up plates 14U and 14L each have inner plate 26, outer frame 28, active electrode 30, connection terminal 32, springs 34a-34d, and spacer member 36. Together pick-up plates 14U and 14L form moveable shared pick-up plate assembly 38. Drive plate 12U and pick-up plate assembly 38 form capacitor 40, while drive plate 12L and pick-up plate assembly 38 form capacitor 42. Drive plates 12U and 12L and pick-up plates 14U and 14L can be substantially square, generally around 12.5 mm square, with the addition of connection terminals 22, 24, and 32. However, it will be understood by one skilled in the art that the dimensions and shape of drive plates 12U and 12L and pick-up plates 14U and 14L can be varied to accommodate different applications. Drive plates 12U and 12L can be made of glass or silicon; pick-up plates 14U and 14L can be made of silicon, including polycrystalline silicon or a single crystal silicon. The benefits of using silicon over metal, as used in the prior art, include improved thermal performance and dimensional tolerance. In general, drive plates 12U and 12L can be manufactured with a wafer of approximately 1.0 mm thickness. Pick-up plates 14U and 14L can generally be manufactured with a wafer of approximately 0.5 mm thickness. In alternative embodiments, thicknesses greater or less than 1.0 mm and 0.5 mm can be used. Additionally, drive plates 12U and 12L and pick-up plates 14U and 14L can be of the same thickness. It will be understood by one skilled in the art that the thickness of drive plates 12U and 12L and pick-up plates 14U and 14L can be varied to accommodate different applications.

Capacitive transducer device 10 can be used in a variety of known applications, including microindentation and microhardness testing, accelerometers, microphones, and other displacement sensors. Motion of shared pick-up plate assembly 38 can be induced (1) by direct mechanical contact with another part attached to capacitive transducer device 10; (2) as a result of inertia of shared pick-up plate assembly 38 when drive plates 12U and 12L are subjected to acceleration in any direction not tangent to the main surface; (3) by electrostatic attraction between shared pick-up plate assembly 38 and fixed drive plates 12U and 12L after voltage is applied to them; and (4) by vibration of the medium the plate is in, e.g., air.

As illustrated in FIG. 1, drive plates 12U and 12L each have active electrode 16 positioned at an inner surface and connected to terminal 22 (shown on drive plate 12L). In one embodiment, active electrode 16 can be approximately 7.9 mm square and positioned centrally on the inner surfaces of drive plates 12U and 12L. Shield electrode 18 can form a partial perimeter around active electrode 16 and can connect to terminal 24. Shield electrode 18 can have a width less than a distance from active electrode 16 to a perimeter of drive plates 12U and 12L. In one embodiment, shield electrode 18 is located approximately 0.8 mm from the perimeter of drive plates 12U and 12L such that shield electrode 18 is positioned inward of spacer member 36 when assembled. Shield electrode 20 can cover the outer surface of drive plates 12U and 12L and can also connect to terminal 24. Connection terminal 22 can connect active electrode 16 to a circuit, while connection terminal 24 can connect shield electrodes 18 and 20 to the circuit. Shield electrodes 18 and 20 can be connected to a ground of a signal conditioning circuit (not shown) to reduce electromagnetic interference (EMI) noise, as known in the art.

Pick-up plates 14U and 14L each have active electrode 30 (shown on pick-up plate 14U). Active electrode 30 can be located on an outer surface to face active electrode 16 on respective drive plates 12U and 12L. Active electrode 30 can be substantially the same dimensions as active electrode 16 and centrally positioned as active electrode 16 is, partially or completely covering the outer surface of inner plate 26. Lead 44 can connect active electrode 30 to connection terminal 32. Lead 44 can follow spring 34a and a portion of an inner perimeter of outer frame 28 to connection terminal 32. Lead 44 can have a width substantially equal to or less than a width of spring 34a. Lead 44 can be deposited on more than one spring for improved symmetry of capacitive transducer device 10. Active electrodes 30 of pick-up plates 14U and 14L can be connected to form a single electrode for shared pick-up plate assembly 38, which is common to both capacitors 40 and 42. In one embodiment, active electrodes 30 can be connected within the structure of capacitive transducer device 10. In another embodiment, the electrical connection can be external to capacitive transducer device 10.

Active electrodes 16 and 30, connection terminals 22, 24, and 32, and shield electrodes 18 and 20 can be a conducting material, including but not limited to aluminum. Active electrodes 16 and 30, connection terminals 22, 24, and 32, and shield electrodes 18 and 20 can be a metalized surface of the silicon or glass substrate fabricated by depositing the conductive material on the substrate using conventional metallization techniques, including but not limited to physical vapor deposition, such as sputtering. In one embodiment, a thickness of active electrodes 16 and 30, connection terminals 22, 24, and 32, and shield electrodes 18 and 20 can be 1 μm.

Spacer members 36, located on the outer surfaces of pick-up plates 14U and 14L, can be bonded to drive plates 12U and 12L and can create a gap between active electrodes 30 and active electrodes 16. Inner surfaces of pick-up plates 14U and 14L can be bonded to form shared pick-up plate assembly 38. Shared pick-up plate assembly 38 is suspended by springs 34a-34d on pick-up plates 14U and 14L to allow parallel movement of active electrodes 30 on pick-up plates 14U and 14L relative to active electrodes 16 on drive plates 12U and 12L. Parallel motion can stabilize the total gap between drive plates 12U and 12L and shared pick-up plate assembly 38 and permit more accurate measurement. Electrical output of capacitive transducer device 10 corresponds to a measurement of a closest distance between active electrodes 16 and 30, which can result from the movement of shared pick-up plate assembly 38 relative to drive plates 12U and 12L. If capacitive transducer device 10 were designed in a manner that allowed a portion of shared pick-up plate assembly 38 to tilt in relation to drive plates 12U and 12L, the closest distance between active electrodes 16 and 30 could be smaller than what would be expected with parallel motion alone, and could yield an incorrectly high electrical output reading. To avoid incorrect output readings, capacitive transducer 10 is designed to provide a means for parallel motion, while limiting or eliminating the potential for tilting motion during operation.

Drive plates 12U and 12L and pick-up plates 14U and 14L each can include a centrally located hole 46 and 48, respectively, for holding a screw, which allows for the installation of a microindentor for hardness testing or a sample holder (motion transfer member). Holes 46 through drive plates 12U and 12L can be larger in diameter than holes 48 through pick-up plates 14U and 14L to allow movement of shared pick-up plate assembly 38 in relation to drive plates 12U and 12L. In one embodiment, holes 46 can be 2.5 mm in diameter; whereas holes 48 can be 0.8 mm in diameter. Holes 46 can include a seal to prevent entry of debris without impeding movement. For other applications, including a force or position sensor, holes may extend only through drive plate 12U and/or 12L. In such configurations where a hole does not extend through shared pick-up plate assembly 38, a sample holder can be inserted into hole 46. A sample exerting a force on the sample holder can thereby move shared pick-up plate assembly 38 in relation to drive plates 12U or 12L, and the displacement can be measured.

Figure 2A:
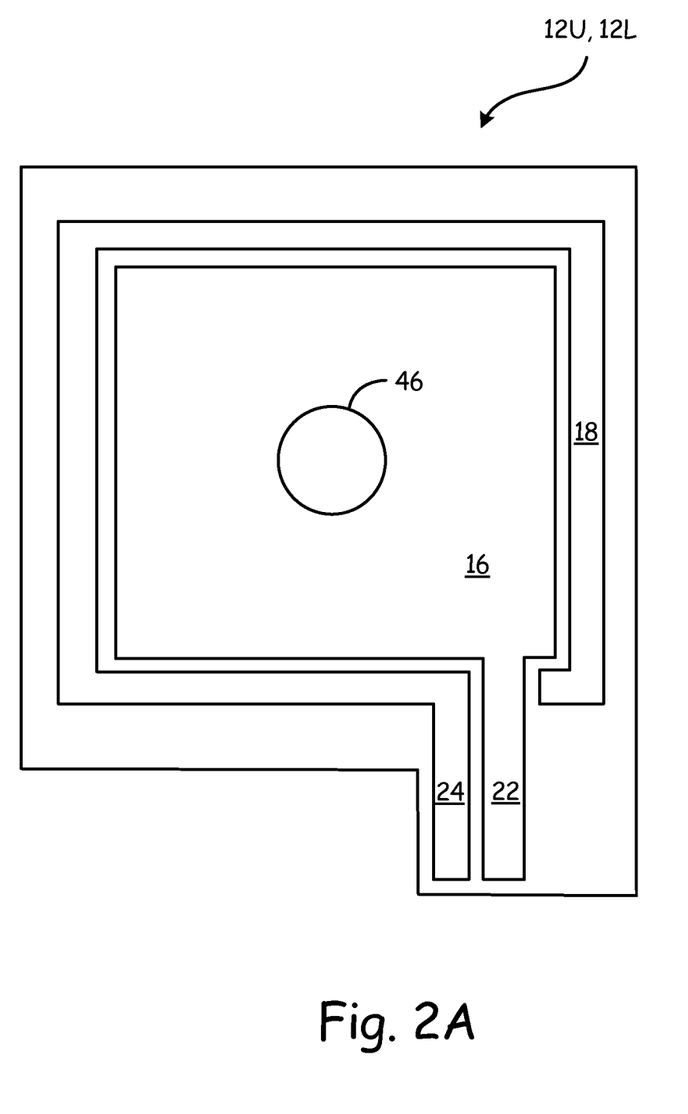
FIG. 2A is a plan view of an inner surface of a drive plate of the capacitive transducer device.
Figure 2B:
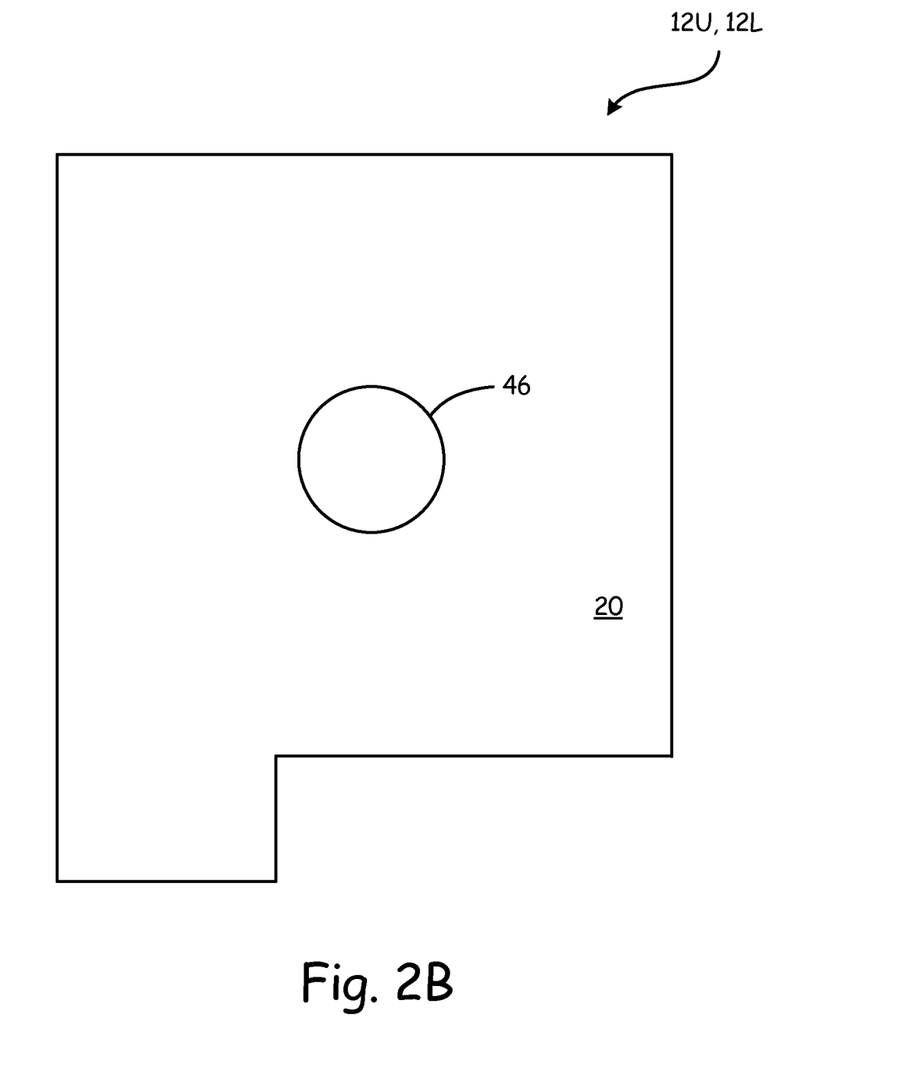
FIG. 2B is a plan view of an outer surface of a drive plate of the capacitive transducer device.

FIGS. 2A and 2B show detailed views of the inner and outer surfaces of drive plates 12U and 12L, respectively. Drive plates 12U and 12L can be duplicates, such that the inner surface of drive plate 12U is substantially the same as the inner surface of drive plate 12L, flipped in orientation for assembly, and the outer surface of drive plate 12L is substantially the same as the outer surface of drive plate 12U, flipped in orientation for assembly. FIG. 2A shows active electrode 16 connected to connection terminal 22; shield electrode 18, forming a perimeter around active electrode 16 and connecting to connection terminal 24; and hole 46, centrally located and extending through drive plate 12U. FIG. 2B shows shield electrode 20, covering the outer surface of drive plate 12L; and hole 46, centrally located and extending through drive plate 12L.

Figure 3A:
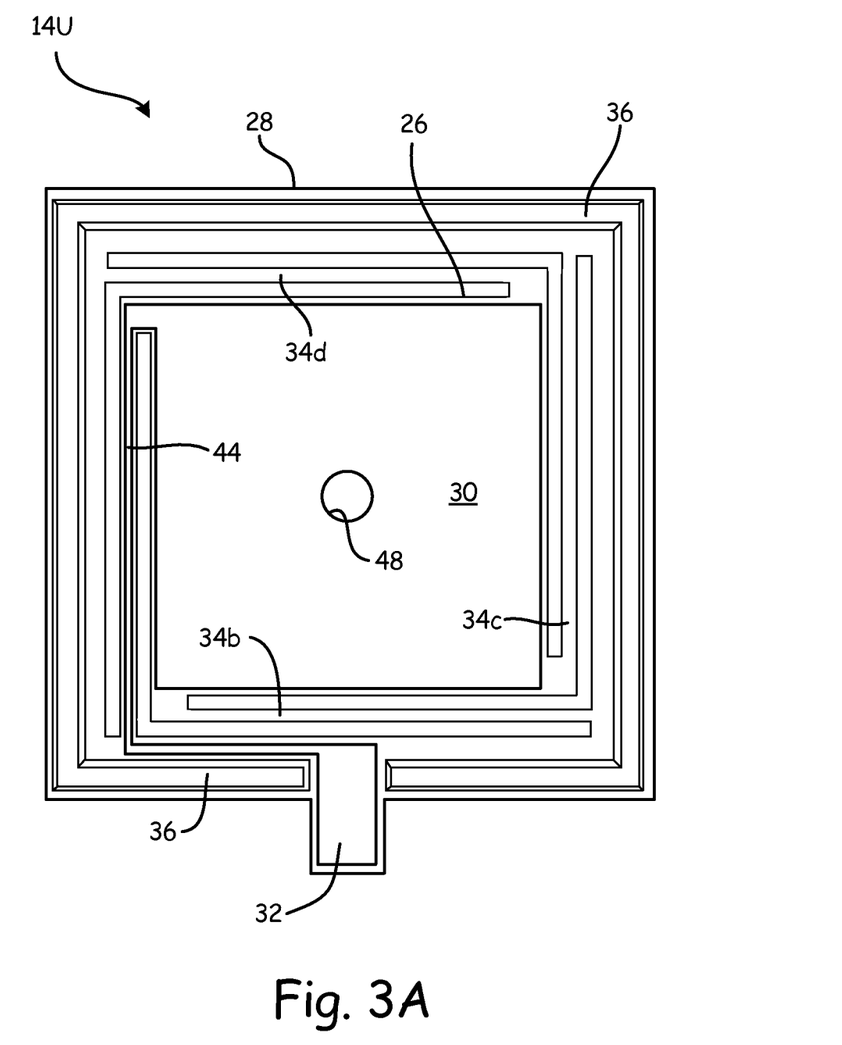
FIG. 3A is a plan view of an outer surface of an upper pick-up plate of the capacitive transducer device.
Figure 3B:
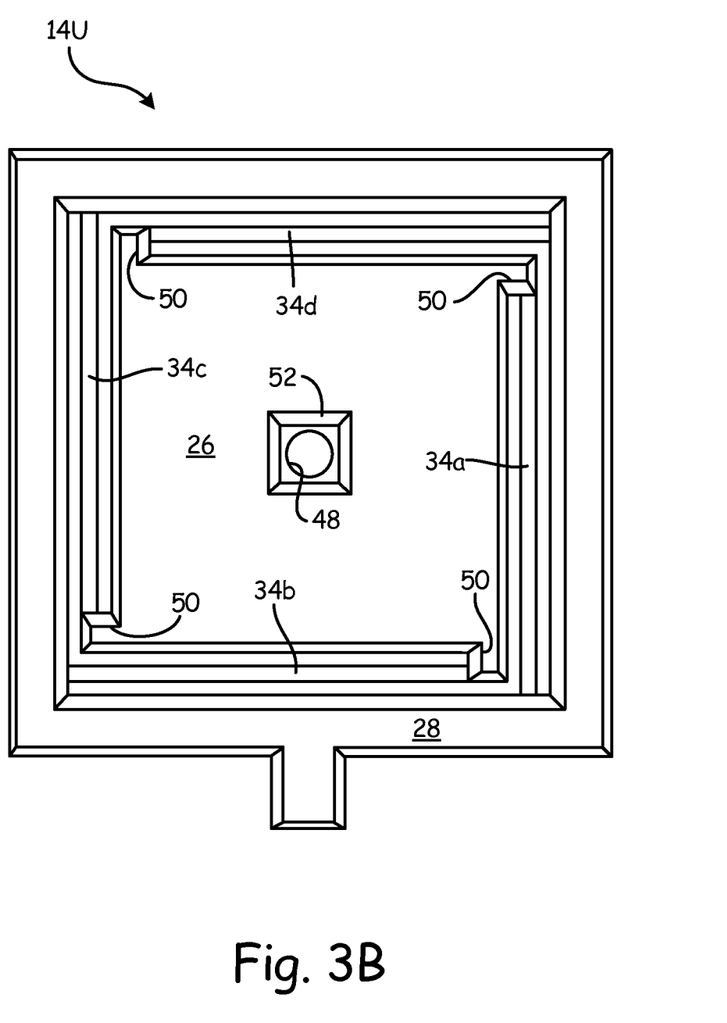
FIG. 3B is a plan view of an inner surface of the upper pick-up plate of the capacitive transducer device.
Figure 4A:
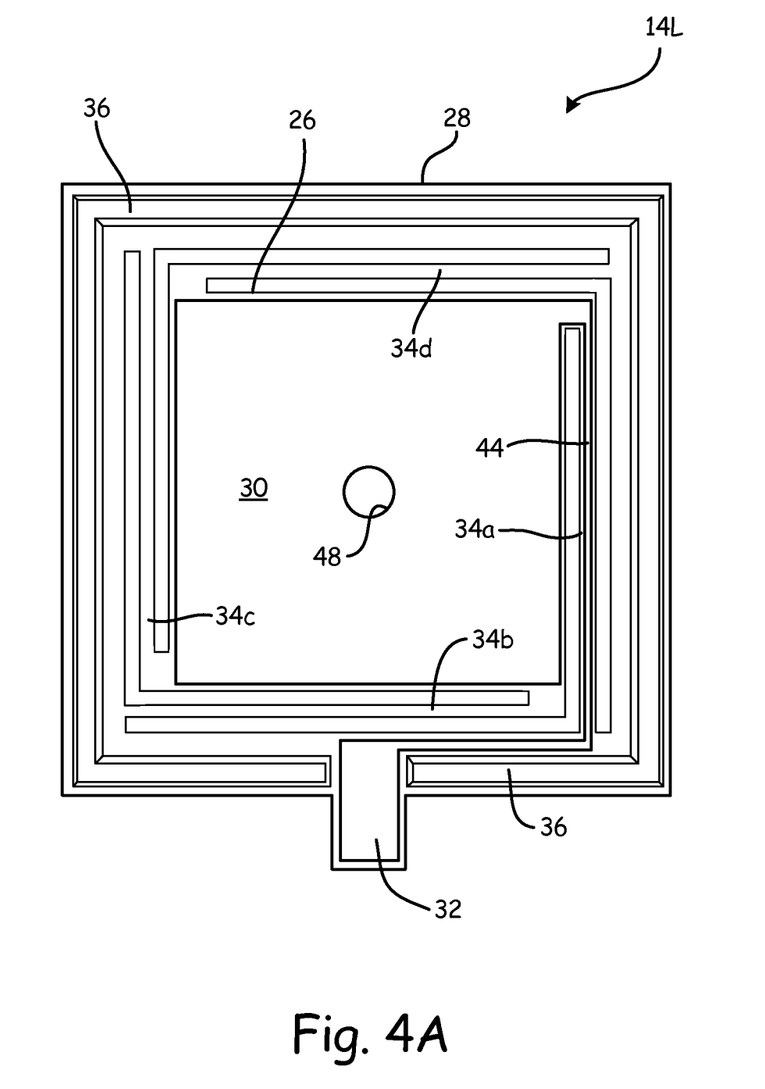
FIG. 4A is a plan view of an outer surface of a lower pick-up plate of the capacitive transducer device.
Figure 4B:
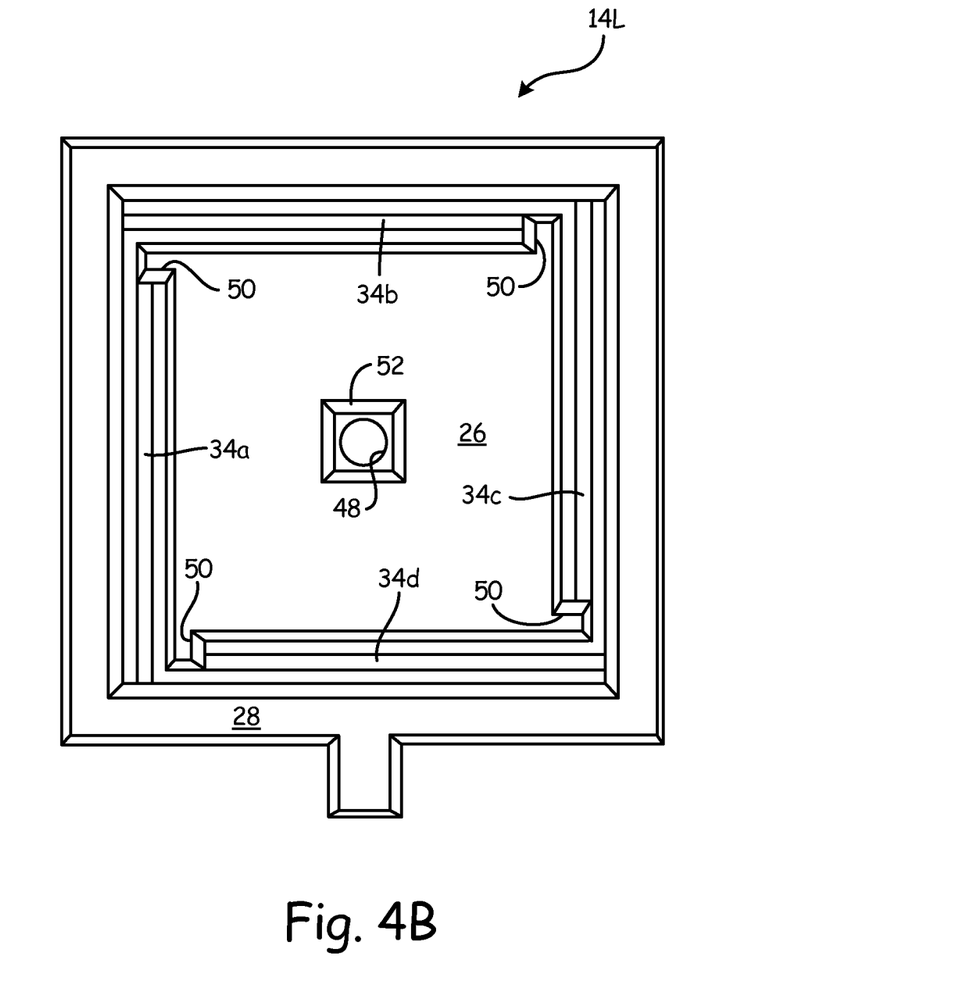
FIG. 4B is a plan view of an inner surface of the lower pick-up plate of the capacitive transducer device.

FIGS. 3A and 3B show detailed views of pick-up plate 14U. FIGS. 4A and 4B show detailed views of pick-up plate 14L. FIG. 3A is a plan view of the outer surface (side A in FIG. 1) of pick-up plate 14U; FIG. 3B is a plan view of the inner surface (side B in FIG. 1) of pick-up plate 14U. Outer frame 28 can be positioned outward of a perimeter of inner plate 26 and connected to inner plate 26 by springs 34a-34d. In one embodiment, inner plate 26 is approximately 9.7 mm square, substantially matching the dimensions of active electrode 16 of drive plates 12U and 12L (shown on drive plate 12L in FIG. 1).

FIG. 3A shows active electrode 30, connection terminal 32, spacer member 36, and lead 44. Spacer member 36 can follow the perimeter of outer frame 28, leaving an opening for connection terminal 32. Spacer member 36 can have a width less than a width of outer frame 28 and can be located adjacent an outer perimeter of outer frame 28 so that spacer member 36 is positioned outward of lead 44 (and outward of second shield electrode 20 of drive plate 12U (FIG. 1) upon assembly). Generally, spacer member 36 can have a width of approximately 0.6 mm at the base of the substrate and can be spaced approximately 0.2 mm from the outer perimeter of outer frame 28. Spacer member 36 can be an insulator or material covered with an insulating coating. Importantly, spacer member 36 is integral with pick-up plate 14U. Prior art devices required a separate spacer member, generally an insulator or metal covered with an insulating layer, which required additional processing as well as additional steps in assembly. Making spacer members 36 integral with pick-up plates 14U and 14L reduces the number of interfaces requiring bonding and reduces the number of substrates, which simplifies assembly. In one embodiment, spacer member 36 is formed by applying a mask to the area of spacer member 36 and etching the full outer surface of pick-up plate 14U to remove a thickness around the masked spacer member 36. Spacer member 36 can be manufactured using conventional wet and/or dry etching techniques. Wet etching generally creates structures with tapered edges as shown on spacer member 36. Wet etching may be preferable over other etching techniques because it is relatively fast and inexpensive, however, other techniques may be used. It will be understood by one skilled in the art that the structured edges of spacer member 36 do not contribute to the functionality of capacitive transducer device 10 and thus can be modified in accordance with the etching technique used.

As previously discussed, spacer member 36 serves to separate active electrode 16 of drive plate 12U from active electrode 30 of pick-up plate 14U. The gap created between active electrodes 16 and 30 can be increased or decreased in distance by the movement of shared pick-up plate assembly 38. In one embodiment, spacer member 36 can have a thickness of approximately 0.1 mm, thereby creating a gap substantially equal to 0.1 mm, less a thickness of active electrodes 16 and 30, between the drive plate 12U and pick-up plate 14U when shared pick-up plate assembly 38 is centrally positioned between drive plates 12U and 12L. It will be understood by one skilled in the art that the thickness of spacer member 36 can be increased or reduced for optimal performance. In an alternative embodiment, a spacer member can additionally be located on drive plates 12U and 12L or can be solely located on drive plates 12U and 12L.

FIG. 3B shows a detailed construction of the suspension assembly of pick-up plate 14U, including inner plate 26, outer frame 28, and springs 34a-34d. Inner plate 26, outer frame 28, and springs 34a-34d can be manufactured as a unit by etching through a full thickness of the silicon substrate between springs 34a-34d and inner plate 26 and between springs 34a-34d and outer frame 28. Conventional etching techniques, such as wet etching can be used in the manufacture of pick-up plate 14U. As previously discussed, conventional wet etching creates structures with tapered edges as shown in FIG. 3B, however, it will be understood by one skilled in the art that the structured edges of shared pick-up plate 14U do not contribute to the functionality of capacitive transducer device 10 and thus can be modified in accordance with the etching technique used.

Springs 34a-34d can be L-shaped and positioned such that one spring emanates from each side of the inner perimeter of outer frame 28 and extends along a length of inner plate 26 before turning to join inner plate 26, creating tab 50. The width of the gaps created by springs 34a-34d between springs 34a-34d and inner plate 26 and springs 34a-34d and outer frame 28 can be substantially equal such that springs 34a-34d are substantially centered between inner plate 26 and outer frame 28. The width of springs 34a-34d can be substantially equal to, or larger or smaller than, the width of the gaps between springs 34a-34d and inner plate 26 and between springs 34a-34d and outer frame 28. Reducing the size of the gaps can increase a surface area available for active electrode 30, which can be beneficial. In one embodiment, the width of springs 34a-34d is approximately 0.2 mm.

Springs 34a-34d can be reduced in thickness to achieve a desired spring constant. Springs 34a-34d can be reduced in thickness by conventional etching techniques, such as wet etching and dry etching. Generally, springs 34a-34d can be wet etched to the desired thickness and then dry etched to achieve the desired spring geometry. The thickness of springs 34a-34d can be reduced from the inner surface of pick-up plate 14U. In one embodiment, the thickness of springs 34a-34d can be approximately 75 µm. Because of the manufacturing methods currently available, springs 34a-34d can be manufactured with a thickness of +/−5 µm or +/−6.67% of the 75 µm thickness of springs 34a-34d. Tolerances of +/−6.67% can result in a variation of spring stiffness of +/−20% and are an improvement over prior art devices incorporating metal springs, which generally have tolerances of +/−10% and spring stiffness variation up to +/−30%. Springs 34a-34d can be reduced in thickness along a long end of the L-shape. The short ends of L-shaped springs 34a-34d, comprising tabs 50, can be of a same thickness as inner plate 26. In another embodiment, springs 34a-34d can be reduced in thickness along the entire L-shape. In yet another embodiment, springs 34a-34d can share a plane with inner plate 26, outer frame 28, and tabs 50. Where springs 34a-34d share a plane with inner plate 26, outer frame 28, and tabs 50, the thickness of the entire pick-up plate 14U is reduced or is selected from a variety of substrate thicknesses to achieve the desired spring constant. Manufacturing of springs 34a-34d from a silicon substrate in the manner illustrated in FIG. 3B and described herein, allows for tighter manufacturing tolerances and creates springs that are less sensitive to deformation during the manufacturing process than the metal springs of prior art devices.

FIG. 3B also illustrates the construction of hole 48. In the embodiment shown, wet etching is used to make a square-shaped partial etch 52 (reduced thickness) around the position of hole 48. Plasma etching is then used to produce the straight edge and circular shape of hole 48 needed to hold a screw or sample holder. Alternatively, plasma etching alone, or other methods allowing for a rounded shape, can be used to create hole 48 (as can be done for hole 46 on drive plates 12U and 12L).

FIG. 4A is a plan view of the outer surface of pick-up plate 14L (side A in FIG. 1). The outer surface of pick-up plate 14L can be a mirror image of the outer surface of pick-up plate 14U, including inner plate 26, outer frame 28, active electrode 30, connection terminal 32, springs 34a-34d, spacer member 36, lead 44, and hole 48. Spacer member 36 separates active electrode 30 on pick-up plate 14L from active electrode 16 on drive plate 12L. Lead 44 can be located on spring 34a or more than one spring (34a-34d) to connect active electrode 30 to connection terminal 32.

FIG. 4B is a plan view of the inner surface of pick-up plate 14L (side B in FIG. 1). The inner surface of pick-up plate 14L can be a mirror image of the inner surface of pick-up plate 14U, including inner plate 26, outer frame 28, springs 34a-34d, hole 48, and tabs 50. Pick-up plate 14L can be manufactured in substantially the same manner as pick-up plate 14U.

Figure 5:
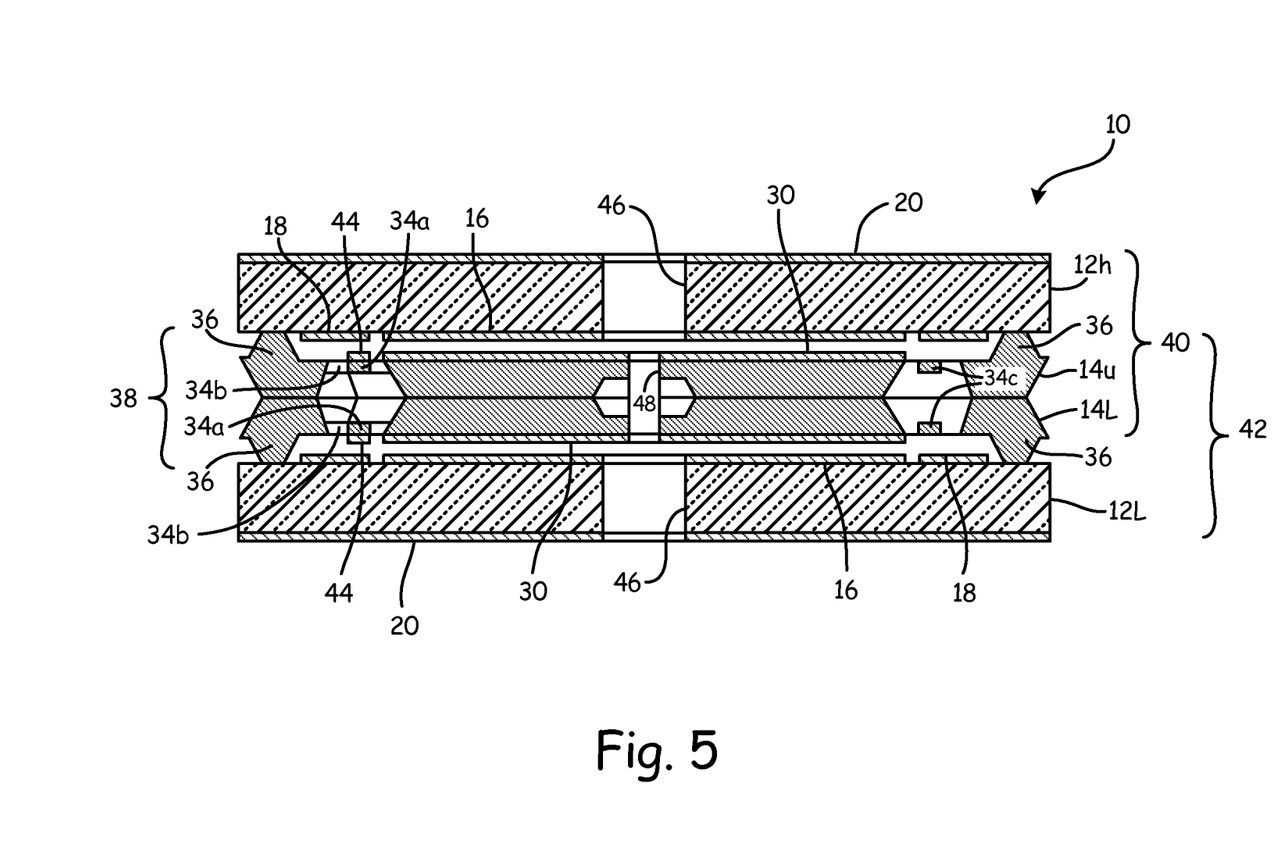
FIG. 5 is a cross-sectional view of the assembled capacitive transducer device taken along the 5-5 line of FIG. 1.

FIG. 5 is a cross-section of assembled capacitive transducer 10 taken along the 5-5 line of FIG. 1. Assembly can be done using conventional methods, allowing the manufacture of multiple capacitive transducer devices 10 in a single process. Generally, a single silicon or glass wafer can be used to manufacture an array of any one plate (12U, 12L, 14U, 14L). For example, a single wafer can comprise multiple drive plates 12U. Each plate (12U, 12L, 14U, 14L) can be suspended on thin bridges intended to hold each plate in place on the wafer during the assembly process. The four wafers, each comprising a different layer of capacitive transducer device 10 as described above, can be stacked and the layers joined with glass frit bonding.

Specifically, pick-up plates 14U and 14L are assembled by bonding the inner surfaces of inner plates 26 and outer frames 28. Drive plates 12U and 12L are joined to pick-up plates 14U and 14L, as shared pick-up plate assembly 38, by bonding spacing members 36 to the inner surface of drive plates 12U and 12L. As shown in FIG. 5, a gap exists between springs 34a-34d on pick-up plate 14U and springs 34a-34d on pick-up plate 14L when the thickness of each spring is reduced from the inner surface of pick-up plates 14U and 14L. The configuration of the two layers of springs provides for parallel motion of shared pick-up plate assembly 38 with respect to drive plates 12U and 12L in transducers 40 and 42. Glass frit bonding is known in the art and can offer advantages over the epoxy adhesive bonding and brazing techniques used in prior art devices comprising metal or metalized ceramic plates. Some of the advantages of glass frit bonding include improved strength, topography tolerance, heat tolerance, and reduced moisture sensitivity.

Each wafer can possess alignment features to aid in the stacking and laminating processes to create complete assemblies. Alignment features can be optical to allow alignment with an optical device, such as a microscope, or can be mechanical. Once the layers are assembled, the bridges holding the individual plates in place on each wafer can be removed to free the assembled capacitive transducer devices 10 from the wafer assembly. Bridges can be broken or cut with an appropriate saw, such as a diamond saw, or other device or separation method known in the art.

Discussion of Possible Embodiments

The following are non-exclusive descriptions of possible embodiments of the present invention.

A capacitive transducer includes a first fixed outer plate having a first fixed electrode positioned on an inner surface, a second fixed outer plate having a second fixed electrode positioned on an inner surface, and a center plate assembly positioned between the first and second fixed outer plates. The center plate assembly includes a top center plate and bottom center plate. The top center plate has a first inner section, a first outer frame positioned outward of a perimeter of the first inner section, a first set of springs connecting the first outer frame to the first inner section, and a first center electrode positioned on an outer surface of the first inner section. The first set of springs has thickness less than each of the first inner section and the first outer frame. The bottom plate is a mirror image of the top center plate including a second inner section, a second outer frame positioned outward of a perimeter of the second inner section, a second set of springs connecting the second outer frame to the second inner section, and a second center electrode positioned on an outer surface of the second inner section. The second center electrode and the first center electrode are connected to become electrically one electrode.

The capacitive transducer of the preceding paragraph can optionally include, additionally and/or alternatively, any one or more of the following features, configurations and/or additional components:

The center plate assembly can be comprised of a silicon substrate and the first and second outer frames can include a first and second spacer member, respectively, wherein the first spacer member extends upward from an outer surface of the first outer frame to separate the first center electrode from the first fixed electrode, and the second spacer member extends downward from an outer surface of the second outer frame to separate the second center electrode from the second fixed electrode, and wherein the first and second spacer members are integral with the first and second outer frames, respectively formed by etching the silicon substrate.

The first and second spacer members can have a width less than a width of each of the first and second outer frames, and wherein the first and second spacer members are located in closer proximity to an outer perimeter of the first and second outer frame than to an inner perimeter of the first and second outer frames.

The first and second fixed outer plates can each further include an outer and inner shield electrode, wherein the outer shield electrodes cover an outer surface of each of the first and second fixed outer plates and the inner shield electrodes form a partial perimeter around the first and second electrodes and are positioned inward of the respective spacer members upon assembly.

The first and second spacer members can have a thickness greater than the thickness of the first and second set of springs, respectively, and less than the thickness of each of the first and second outer frame and first and second inner section.

The inner section of the top center plate can further include a plurality of tabs, each of the plurality of tabs extending from a different corner of the first inner section toward the first outer frame.

The first set of springs can comprise a plurality of springs, each of the plurality of springs emanating from a different side of an inner perimeter of the first outer frame and extending along a length of the first inner section before joining a tab of the first inner section.

The thickness of the plurality of springs can be reduced from an inner surface of the top center plate, and wherein an outer surface of the plurality of springs shares a plane with a portion of the outer surface of the plurality of tabs and the first outer frame.

The top center plate can further include a connection terminal extending from the outer frame and an electrical lead connecting the first center electrode to the connection terminal. The electrical lead can be deposited on the outer surface of at least one spring within the first set of springs.

Each spring within the first set of springs can be substantially centered between the first inner section and the first outer frame.

The first and second fixed outer plates and the top and bottom center plates of the center plate assembly can each further include a centrally located hole that extends through a full thickness of the plate, wherein the hole in each of the top and bottom center plates can have a diameter smaller than a diameter of the hole in each of the first and second fixed outer plates.

The first and second fixed electrodes and first and second center electrodes can each comprise a layer of conducting material that has been deposited on the first fixed outer plate, second fixed outer plate, top center plate, and bottom center plate, respectively.

A capacitive transducer includes a first fixed outer plate having a first fixed electrode positioned on an inner surface, a second fixed outer plate having a second fixed electrode positioned on an inner surface, and a center plate assembly positioned between the first and second fixed outer plates. The center plate assembly includes a top center plate and a bottom center plate. The top center plate includes a first inner section, a first outer frame positioned outward of a perimeter of the first inner section, a first set of springs connecting the first outer frame to the first inner section, a first center electrode positioned on an outer surface of the first inner section, and a first spacer member extending upward from an outer surface of the first outer frame to separate the first center electrode from the first fixed electrode. The bottom center plate is a mirror image of the top center plate including a second inner section, a second outer frame positioned outward of a perimeter of the second inner section, a second set of springs connecting the second outer frame to the second inner section, a second center electrode positioned on an outer surface of the second inner section, and a second spacer member extending downward from an outer surface of the second outer frame to separate the second center electrode from the second fixed electrode. The second center electrode and the first center electrode are connected to become electrically one electrode. An inner surface of the top center plate and an inner surface of the bottom center plate are bonded together.

The capacitive transducer of the preceding paragraph can optionally include, additionally and/or alternatively, any one or more of the following features, configurations and/or additional components:

The top center plate and the bottom center plate can each be comprised of a silicon substrate, and the first and second spacer members can be integral with the top and bottom center plates, respectively, formed by etching the silicon substrate.

The first set of springs can have a thickness less than a thickness of each of the first spacer member, first outer frame, and first inner section and wherein the first set of springs shares a plane with a portion of the outer surface of the first outer frame.

The inner section of the top center plate can further include a plurality of tabs, each of the plurality of tabs extending from a different corner of the first inner section toward the first outer frame.

The first set of springs can comprise a plurality of springs, each of the plurality of springs emanating from a different side of an inner perimeter of the first outer frame and extending along a length of the first inner section before joining a tab of the first inner section.

The first spacer member can have a thickness greater than the thickness of the first set of springs and less than the thickness of each of the first outer frame and first inner section.

A method of making a capacitive transducer includes the steps of etching an outer surface of each of an upper and lower center plate to form a raised spacer member along a perimeter of the upper and lower center plates; etching through a full thickness of each of the upper and lower center plates to create an outer frame, inner section, and a plurality of springs connecting the outer frame to the inner section; depositing a layer of conducting material on the outer surface of the inner section of each of the upper and lower center plates; depositing a layer of conducting material on an inner surface of a first fixed outer plate and an inner surface of a second fixed outer plate; etching through a full thickness of a portion of each of the upper and lower center plates and the first and second fixed outer plates to create a centrally-located hole; glass frit bonding the first and second center plates together; and glass frit bonding the spacer members to inner surfaces of the first and second fixed outer plates.

The method of the preceding paragraph can further include the steps of etching through a partial thickness of the plurality of springs to reduce a thickness of the plurality of springs, and depositing a layer of conducting material on an outer surface of the first and second fixed outer plates.

Summation

Any relative terms or terms of degree used herein, such as "substantially", "essentially", "generally", "approximately" and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, alignment or shape variations induced by thermal, rotational or vibrational operational conditions, and the like.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A capacitive transducer comprising:
   a first fixed outer plate having a first fixed electrode positioned on an inner surface;
   a second fixed outer plate having a second fixed electrode positioned on an inner surface; and
   a center plate assembly positioned between the first and second fixed outer plates, the center plate assembly comprising:
     a top center plate comprising:
       a first silicon substrate;
       a first inner section of the first silicon substrate;
       a first outer frame of the first silicon substrate positioned outward of a perimeter of the first inner section, wherein a first raised spacer member is integrally formed with the first outer frame and extends upward from an outer surface of the first outer frame;
       a first set of springs of the first silicon substrate connecting the first outer frame to the first inner section, wherein the first set of springs has thickness less than each of the first inner section and the first outer frame; and
       a first center electrode positioned on an outer surface of the first inner section; and
     a bottom center plate comprising:
       a second silicon substrate;
       a second inner section of the second silicon substrate;
       a second outer frame of the second silicon substrate positioned outward of a perimeter of the second inner section, wherein a second raised spacer member is integral with the second outer frame and extends downward from an outer surface of the second outer frame;
       a second set of springs of the second silicon substrate connecting the second outer frame to the second inner section, wherein the second set of springs has a thickness less than each of the second inner section and the second outer frame;
       a second center electrode positioned on an outer surface of the second inner section, wherein the second center electrode and the first center electrode are connected to form a single electrode, and wherein the bottom center plate is a mirror image of the top center plate.

2. The capacitive transducer of claim 1, wherein the first and second spacer members each have a width less than a width of each of the first and second outer frames, and wherein the first and second spacer members are located in closer proximity to an outer perimeter of the first and second outer frames than to an inner perimeter of the first and second outer frames.

3. The capacitive transducer of claim 2, wherein the first and second fixed outer plates each further comprise:
   an outer and inner shield electrode, wherein the outer shield electrodes cover an outer surface of each of the first and second fixed outer plates and the inner shield electrodes form a partial perimeter around the first and second fixed electrodes and are positioned inward of the respective spacer members upon assembly.

4. The capacitive transducer of claim 1, wherein the first and second spacer members each have a thickness greater than the thickness of the first and second set of springs, respectively, and less than the thickness of each of the first and second outer frames and first and second inner sections.

5. The capacitive transducer of claim 1, wherein the first inner section further comprises:
   a plurality of tabs, each of the plurality of tabs extending from a different corner of the first inner section toward the first outer frame.

6. The capacitive transducer of claim 5, wherein the first set of springs comprises a plurality of springs, each of the plurality of springs emanating from a different side of an inner perimeter of the first outer frame and extending along a length of the first inner section before joining a tab of the first inner section.

7. The capacitive transducer of claim 6, wherein the thickness of the first set of springs is reduced from an inner surface of the top center plate, and wherein an outer surface of the first set of springs shares a plane with a portion of the outer surface of the plurality of tabs and the first outer frame.

8. The capacitive transducer of claim 7, wherein the top center plate further comprises:
   a connection terminal extending from the first outer frame; and
   an electrical lead connecting the first center electrode to the connection terminal, wherein the electrical lead is deposited on the outer surface of at least one spring within the first set of springs.

9. The capacitive transducer of claim 7, wherein each spring within the first set of springs is substantially centered between the first inner section and the first outer frame.

10. The capacitive transducer of claim 1, wherein the first and second fixed outer plates and the top and bottom center plates of the center plate assembly each further comprise:
    a centrally located hole that extends through a full thickness of the plate, wherein the hole in each of the top and bottom center plates has a diameter smaller than a diameter of the hole in each of the first and second fixed outer plates.

11. The capacitive transducer of claim 1, wherein the first and second fixed electrodes and first and second center electrodes each comprise a layer of conducting material that has been deposited on the first fixed outer plate, second fixed outer plate, top center plate, and bottom center plate, respectively.

12. A capacitive transducer comprising:
a first fixed outer plate having a first fixed electrode positioned on an inner surface;
a second fixed outer plate having a second fixed electrode positioned on an inner surface;
a center plate assembly positioned between the first and second fixed outer plates and comprising:
a top center plate comprising:
a first silicon substrate;
a first inner section of the first silicon substrate;
a first outer frame of the first silicon substrate positioned outward of a perimeter of the first inner section, wherein a first raised spacer member is integrally formed with the first outer frame and extends upward from an outer surface of the first outer frame;
a first set of springs of the first silicon substrate connecting the first outer frame to the first inner section; and
a first center electrode positioned on an outer surface of the first inner section; and
a bottom center plate comprising:
a second silicon substrate;
a second inner section of the second silicon substrate;
a second outer frame of the second silicon substrate positioned outward of a perimeter of the second inner section, wherein a second raised spacer member is integrally formed with the second outer frame and extends downward from an outer surface of the second outer frame;
a second set of springs of the second silicon substrate connecting the second outer frame to the second inner section; and
a second center electrode positioned on an outer surface of the second inner section, wherein the second center electrode and the first center electrode are connected to form a single electrode;
wherein the bottom center plate is a mirror image of the top center plate, and an inner surface of the top center plate and an inner surface of the bottom center plate are bonded together.

13. The capacitive transducer of claim 12, wherein the first set of springs has a thickness less than a thickness of each of the first spacer member, first outer frame, and first inner section, and wherein the first set of springs shares a plane with a portion of the outer surface of the first outer frame.

14. The capacitive transducer of claim 13, wherein the first inner section further comprises:
a plurality of tabs, each of the plurality of tabs extending from a different corner of the first inner section toward the first outer frame.

15. The capacitive transducer of claim 14, wherein the first set of springs comprises a plurality of springs, each of the plurality of springs emanating from a different side of an inner perimeter of the first outer frame and extending along a length of the first inner section before joining a tab of the first inner section.

16. The capacitive transducer of claim 13, wherein the first spacer member has a thickness greater than the thickness of the first set of springs and less than the thickness of each of the first outer frame and first inner section.

17. A method of assembling a capacitive transducer comprising the steps of:
providing silicon substrates to be fabricated as top and bottom center plates;
etching an outer surface of each of a top and bottom center plate to form a raised spacer member along a perimeter of the outer surface of each of the top and bottom center plates;
etching through a full thickness of each of the top and bottom center plates to create an outer frame, inner section, and a plurality of springs connecting the outer frame to the inner section;
depositing a layer of conducting material on an outer surface of the inner section of each of the top and bottom center plates;
depositing a layer of conducting material on an outer surface of at least one of the plurality of springs on each of the top and bottom center plates to connect a center electrode on the inner section to a connection terminal on the outer frame;
depositing a layer of conducting material on an inner surface of a first fixed outer plate and an inner surface of a second fixed outer plate;
etching through a full thickness of a portion of each of the top and bottom center plates and the first and second fixed outer plates to create a centrally-located hole;
glass frit bonding the first and second center plates together; and
glass frit bonding the spacer members to the inner surfaces of the first and second fixed outer plates.

18. The method of claim 17, further comprising the steps of:
etching through a partial thickness of the plurality of springs to reduce a thickness of the plurality of springs, wherein etching comprises removing material from the silicon substrate; and
depositing a layer of conducting material on an outer surface of the first and second fixed outer plates.

* * * * *

UNITED STATES PATENT AND TRADEMARK OFFICE
CERTIFICATE OF CORRECTION

PATENT NO. : 9,752,900 B2
APPLICATION NO. : 14/796266
DATED : September 5, 2017
INVENTOR(S) : Jerzy Wyrobek Page 1 of 1

It is certified that error appears in the above-identified patent and that said Letters Patent is hereby corrected as shown below:

In the Specification

Column 3, Line 21:
Delete "minor"
Insert --mirror--

Column 3, Line 22:
Delete "minor"
Insert --mirror--

Signed and Sealed this
Twentieth Day of February, 2018

Andrei Iancu
*Director of the United States Patent and Trademark Office*